(12) United States Patent
Lim et al.

(10) Patent No.: US 6,358,688 B1
(45) Date of Patent: Mar. 19, 2002

(54) IMMORTALIZED HUMAN MIDDLE EAR EPITHELIAL CELL LINES

(75) Inventors: David J. Lim, Pasadena, CA (US); Young-Myoung Chun, Kyungki-Do (KR); Johng S. Rhim, Potomac, MD (US); Derald E. Brackmann, South Pasadena, CA (US)

(73) Assignee: House Ear Institute, Los Angeles, CA (US)

( * ) Notice: Subject to any disclaimer, the term of this patent is extended or adjusted under 35 U.S.C. 154(b) by 0 days.

(21) Appl. No.: 09/580,189

(22) Filed: May 26, 2000

Related U.S. Application Data

(60) Provisional application No. 60/136,736, filed on May 28, 1999.

(51) Int. Cl.⁷ .................................................. C12Q 1/68
(52) U.S. Cl. ............................ 435/6; 435/467; 435/371
(58) Field of Search ............................. 435/6, 467, 371

(56) References Cited

U.S. PATENT DOCUMENTS 4,885,238 A  * 12/1989  Reddel et al.

OTHER PUBLICATIONS

Kuroki et al., Japanese Journal of Cancer Research, vol. 84, pp. 1091–1100.*

* cited by examiner

*Primary Examiner*—James Ketter
(74) *Attorney, Agent, or Firm*—Fulbright & Jaworski L.L.P.

(57) ABSTRACT

Human middle ear epithelial cell lines permanently transformed by human papilloma viruses have been obtained. These cell lines are useful for the study of gene and protein expression in otitis media and the identification of chemical and biological agents that may be useful in the therapy of human otitis media and other diseases of the ear.

24 Claims, 9 Drawing Sheets

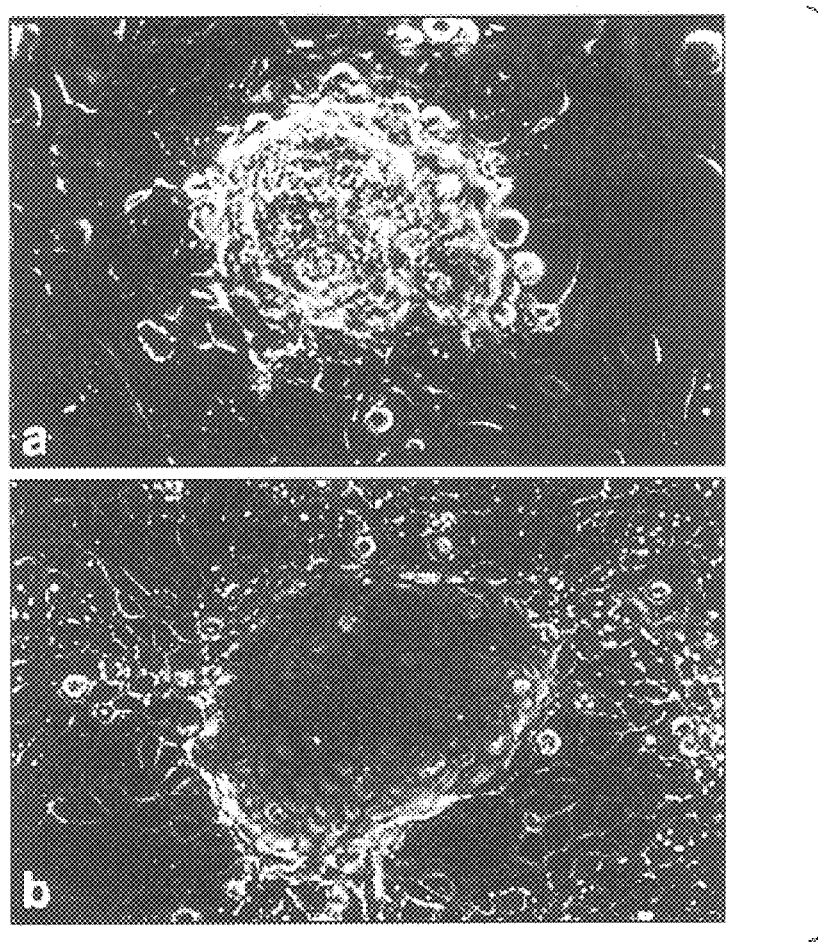
FIG. 1
FIG. 4
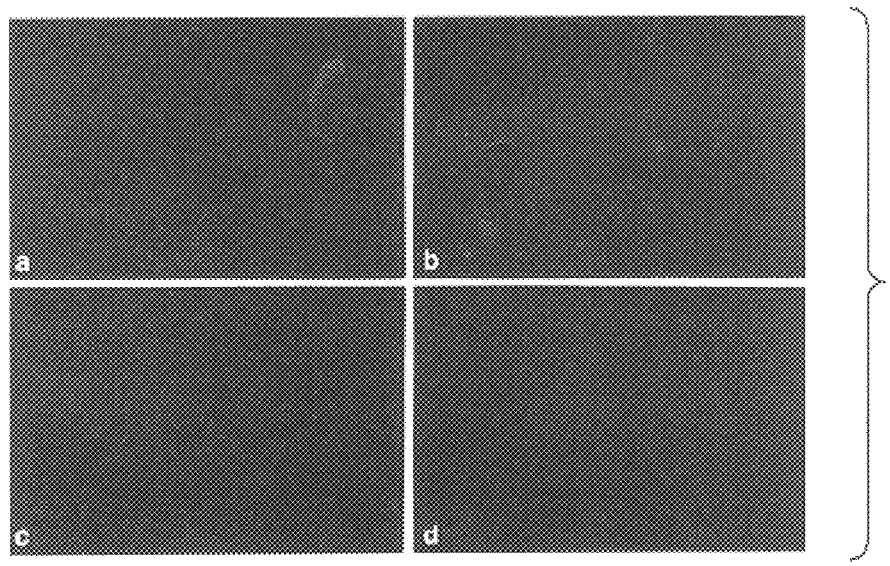

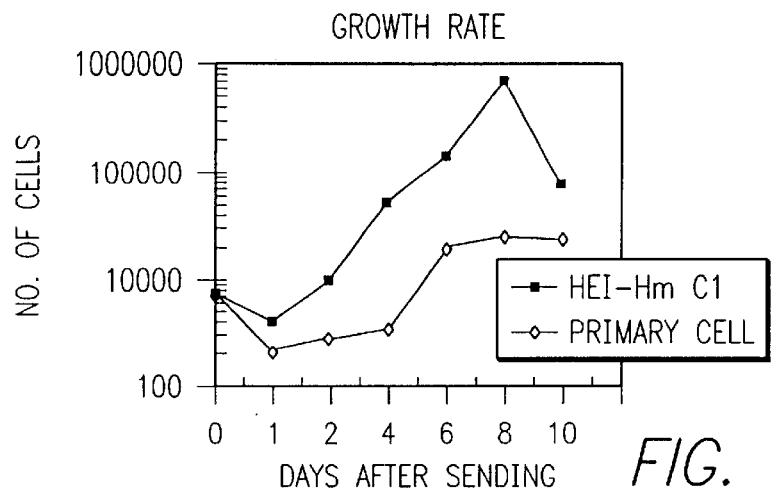
FIG. 2
FIG. 3
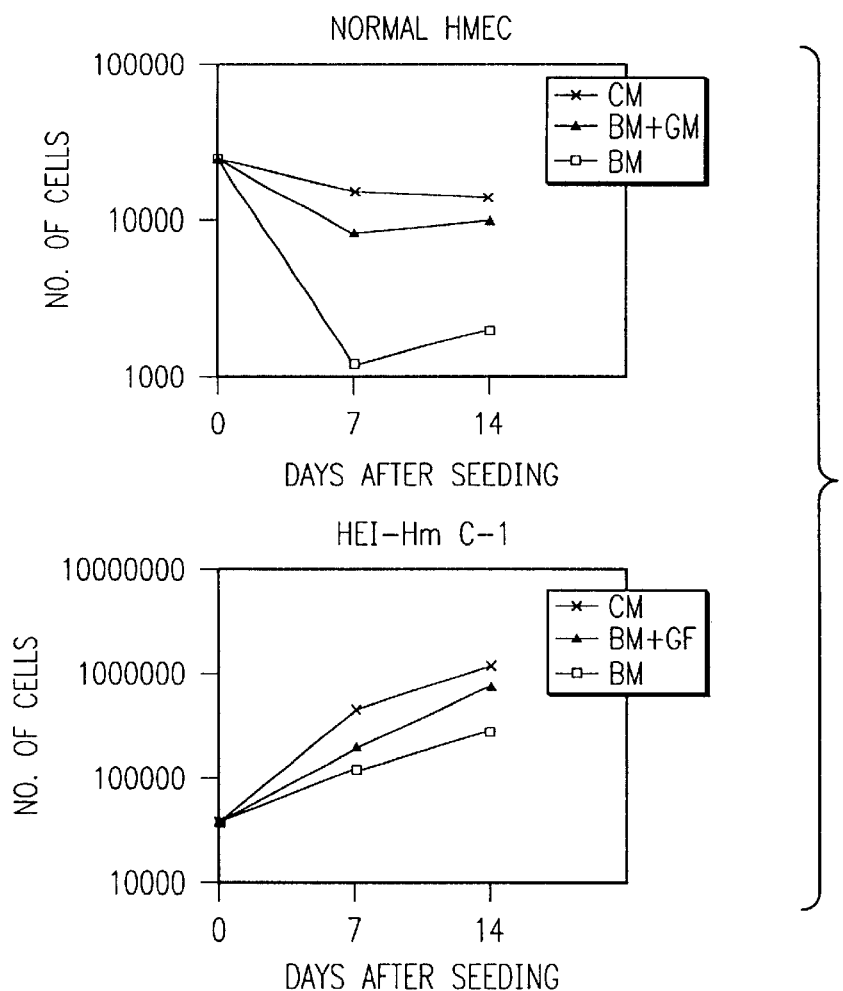

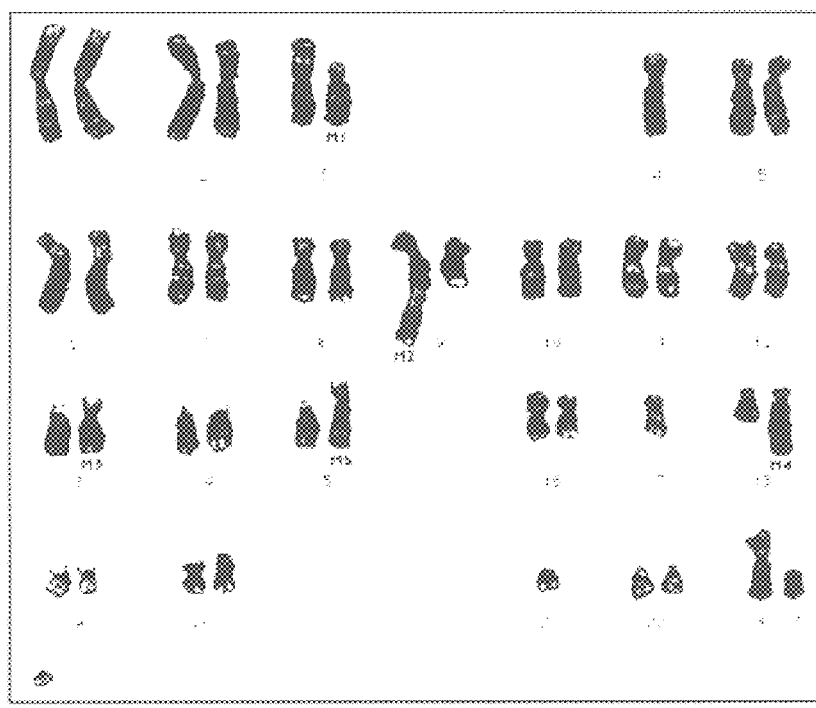
FIG. 12
FIG. 13
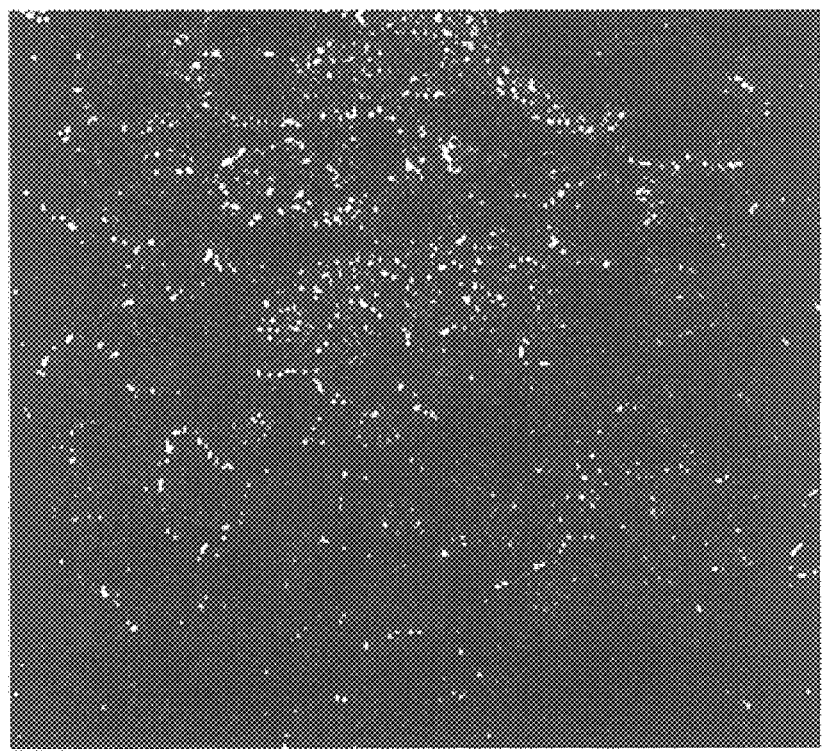

SEQUENCE LISTING

```
<160> NUMBER OF SEQ ID NOS:  24

<210> SEQ ID NO 1
<211> LENGTH: 23
<212> TYPE: DNA
<213> ORGANISM: Human papillomavirus type 16

<400> SEQUENCE: 1
gcaagcaaca gttactgcga cgt                                              23

<210> SEQ ID NO 2
<211> LENGTH: 23
<212> TYPE: DNA
<213> ORGANISM: Human papillomavirus type 16

<400> SEQUENCE: 2
gcaacaagac atacatcgac cgg                                              23

<210> SEQ ID NO 3
<211> LENGTH: 20
<212> TYPE: DNA
<213> ORGANISM: Human papillomavirus type 16

<400> SEQUENCE: 3
gatggtccag ctggacaagc                                                  20

<210> SEQ ID NO 4
<211> LENGTH: 19
<212> TYPE: DNA
<213> ORGANISM: Homo sapiens

<400> SEQUENCE: 4
gtgccattaa caggtcttc                                                   19

<210> SEQ ID NO 5
<211> LENGTH: 20
<212> TYPE: DNA
<213> ORGANISM: Homo sapiens

<400> SEQUENCE: 5
ctcctttctt cctgctgctg                                                  20

<210> SEQ ID NO 6
<211> LENGTH: 20
<212> TYPE: DNA
<213> ORGANISM: Homo sapiens
```

```
<210> SEQ ID NO 6
<211> LENGTH: 20
<212> TYPE: DNA
<213> ORGANISM: Homo sapiens

<400> SEQUENCE: 6
cagctgaacc tgaagctggt                                                    20

<210> SEQ ID NO 7
<211> LENGTH: 18
<212> TYPE: DNA
<213> ORGANISM: Homo sapiens

<400> SEQUENCE: 7
tgcctggccc tgtctttg                                                      18

<210> SEQ ID NO 8
<211> LENGTH: 18
<212> TYPE: DNA
<213> ORGANISM: Homo sapiens

<400> SEQUENCE: 8
cagctccagc atgagtgc                                                      18

<210> SEQ ID NO 9
<211> LENGTH: 20
<212> TYPE: DNA
<213> ORGANISM: Homo sapiens

<400> SEQUENCE: 9
gtcaccaaca ccagcaagag                                                    20

<210> SEQ ID NO 10
<211> LENGTH: 20
<212> TYPE: DNA
<213> ORGANISM: Homo sapiens

<400> SEQUENCE: 10
tcgagcgagt acatggaaga                                                    20

<210> SEQ ID NO 11
<211> LENGTH: 18
<212> TYPE: DNA
<213> ORGANISM: Homo sapiens

<400> SEQUENCE: 11
ccactgtgtg acccacca                                                      18

<210> SEQ ID NO 12
<211> LENGTH: 18
<212> TYPE: DNA
<213> ORGANISM: Homo sapiens

<400> SEQUENCE: 12
tgctgctgga tgatcagg                                                      18

<210> SEQ ID NO 13
<211> LENGTH: 20
<212> TYPE: DNA
<213> ORGANISM: Homo sapiens

<400> SEQUENCE: 13
atgaaacctg ggtcaacagc                                                    20

<210> SEQ ID NO 14
<211> LENGTH: 20
<212> TYPE: DNA
<213> ORGANISM: Homo sapiens
```

```
<400> SEQUENCE: 14
gggcctctgc tgagtacttg                                              20

<210> SEQ ID NO 15
<211> LENGTH: 20
<212> TYPE: DNA
<213> ORGANISM: Homo sapiens

<400> SEQUENCE: 15
tccatcctct ctggtgtgag                                              20

<210> SEQ ID NO 16
<211> LENGTH: 20
<212> TYPE: DNA
<213> ORGANISM: Homo sapiens

<400> SEQUENCE: 16
ccttgactac gctggggaat                                              20

<210> SEQ ID NO 17
<211> LENGTH: 20
<212> TYPE: DNA
<213> ORGANISM: Homo sapiens

<400> SEQUENCE: 17
aaccatttac ggaggcacag                                              20

<210> SEQ ID NO 18
<211> LENGTH: 20
<212> TYPE: DNA
<213> ORGANISM: Homo sapiens

<400> SEQUENCE: 18
cagaactcgc agaccacaag                                              20

<210> SEQ ID NO 19
<211> LENGTH: 23
<212> TYPE: DNA
<213> ORGANISM: Homo sapiens

<400> SEQUENCE: 19
atgagaactt cctaccttct gct                                          23

<210> SEQ ID NO 20
<211> LENGTH: 15
<212> TYPE: DNA
<213> ORGANISM: Homo sapiens

<400> SEQUENCE: 20
tcacttgcag cactt                                                   15

<210> SEQ ID NO 21
<211> LENGTH: 20
<212> TYPE: DNA
<213> ORGANISM: Homo sapiens

<400> SEQUENCE: 21
tttggtggta taggcgatcc                                              20

<210> SEQ ID NO 22
<211> LENGTH: 20
<212> TYPE: DNA
```

```
<213> ORGANISM: Homo sapiens

<400> SEQUENCE: 22
atgtcgcacg tctctgatga                                            20

<210> SEQ ID NO 23
<211> LENGTH: 22
<212> TYPE: DNA
<213> ORGANISM: Homo sapiens

<400> SEQUENCE: 23
ctcgcgctac tctctctttt gg                                         22

<210> SEQ ID NO 24
<211> LENGTH: 25
<212> TYPE: DNA
<213> ORGANISM: Homo sapiens

<400> SEQUENCE: 24
gcttacatgt ctcgatccca cttaa                                      25
```

IMMORTALIZED HUMAN MIDDLE EAR EPITHELIAL CELL LINES

CROSS REFERENCE TO RELATED APPLICATIONS

This application claims the benefit of Provisional Patent Application No. 60/136,736, filed May 28, 1999, which is incorporated herein by reference.

TECHNICAL FIELD OF THE INVENTION

The present invention relates to novel immortalized middle ear epithelial cell lines and their use in screening assays.

BACKGROUND OF THE INVENTION

Otitis media (OM), or inflammation of the middle ear, is the second most frequent illness resulting in visits to physicians following the common cold and the most common cause of hearing impairment in children. According to the Centers for Disease Control and Prevention/National Center for Health Statistics, OM accounts for an estimated 31 million annual visits to the doctor's office. Eighty percent of the children born each year experience at least one episode of OM by their third birthday, and one in three have repeated bouts of the disease. Although the fraction of health care expenditure taken up by OM is unknown, it is estimated to have a yearly cost exceeding $5 billion.

Acute OM (AOM) generally refers to the rapid onset of signs and symptoms of an acute infection in the middle ear. Chronic otitis media with effusion (OME), also known as persistent middle ear effusion, is the major sequela of acute OM. OME is characterized by the accumulation of serous, mucoid or purulent fluid in the middle ear space, without compromising the intactness of the tympanic membrane (Bluestone, C. and Klein, J O. 1995. Otitis media in infants and children: W.B. Saunders Company). In approximately 40% of the cases, middle ear effusion can still be seen one month after antibiotic treatment and in 20% of them, even after three months. In the US alone, about one million tympanostomy tubes are inserted per year, for the treatment of persistent or recurring OM. The course of OME is generally benign and self-limiting. The deafness caused by the effusions, however, if not treated in time, could adversely affect the child's development and educational progress.

OM is caused mainly by three pathogens: *Streptococcus pneumoniae, Moraxella catarrhalis* and non-typeable *Haemophilus influenzae* (NTHI) [Block, S. L. 1997. Causative pathogens, antibiotic resistance and therapeutic considerations in acute otitis media. Pediatr Infect Dis J. 16: 449–56; Brook, I. 1994. Otitis media: microbiology and management. J Otolaryngol. 23: 269–75; Maxson, S., T. Yamauchi. 1996. Acute otitis media. Pediatr Rev. 17: 191–5; and Strausbaugh, L. 1997. Haemophilus influenzae infections in adults: a pathogen in search of respect. Postgrad Med. 101:191–200]. The inflammatory reaction caused by the interaction of bacterial surface components with the epithelial cells of the middle ear is one of the most crucial steps in the development of otitis media. Many of the processes involved however, remain poorly understood [DeMaria, T. F., Yamaguchi, T., Bakaletz, L. O., and Lim, D. J. (1992). Serum and middle ear antibody response in the chinchilla during otitis media with effusion induced by nonviable nontypeable Haemophilus influenzae. J Infect Dis 165, S196-.; Ernst, (1999). Review article: the role of inflammation in the pathogenesis of gastric cancer. Aliment Pharmacol Ther 13, 13–18; Giebink, G. S. (1999). Otitis media: the chinchilla model. Microb Drug Resist 5, 57–72; Patel, J., Faden, H., Sharma, S., and Ogra, P. L. (1992). Effect of respiratory syncytial virus on adherence, colonization and immunity of non-typable Haemophilus influenzae: implications for otitis media. Int J Pediatr Otorhinolaryngol 23, 15–23; and Weinberg, A., Krisanaprakornkit, S., and Dale, B. A. (1998) Epithelial antimicrobial peptides: review and significance for oral applications. Crit Rev Oral Biol Med 9, 399–414]. In order elucidate the cellular and molecular mechanisms involved in the pathogenesis of otitis media, it is important to understand the biology of the middle ear epithelium and such studies have traditionally required large numbers of middle ear epithelial cells. Although there have been several reports on the establishment of primary cultures and cell lines of middle ear epithelial cells in rodents, to date there have been no reports of immortalized human middle ear epithelial cells. Thus, there is a need for cell lines derived from normal human middle ear that can be used, to study the molecular mechanisms involved in the pathogenesis of otitis media.

Primary cultures of untransformed human cells are generally difficult to propagate for extended periods. Their life span in culture is very limited and they usually become senescent after 4–5 passages. Although middle ear and Eustachian tube epithelial cell lines have been derived from laboratory animals [Portier F., et al. Oxygen modulates Na+ absorption in middle ear epithelium. Am J Physiol 1999 Feb;276(2 Pt 1):C312–7; van Blitterswijk C A, et al. Culture and characterization of rat middle-ear epithelium. Acta Otolaryngol (Stockh). 1986 May–Jun; 101 (5–6):453–66; Takeno S, et al. Tissue culture of middle ear epithelium using fibroblast-reorganized collagen gels. J Otolaryngol. 1993 Oct;22(5):3804; de Serres L M, et al. Bioelectric properties of gerbil middle ear epithelia. Arch Otolaryngol Head Neck Surg 1991 Apr;117(4):416–21; Herman P, et al. Ion transport by primary cultures of Mongolian gerbil middle ear epithelium. Am J Physiol 1992 Mar;262(3 Pt 2):F373–80; Ueyama S., et al. Immortalization of rat middle ear epithelial cells by Adenol2-SV40 hybrid. Ann Otol Rhinol Laryngol. (in print); Herman P., et al. Middle ear cell line that maintains vectorial electrolyte transport. J Cell Physiol. 1993 Mar;154 (3):615–22.; and Nakamura A, et al. Serial culture and characterization of the chinchilla middle era epithelium. Ann Otol Rhinol Laryngol. 1991 Dec;100(12): 1024–31.], to date there have been no report of immortailized human middle ear epithelial cells.

Expression of viral genes is an effective way of immortalizing primary cells. Among the most commonly used and effective transforming viral sequences are the E6 and E7 genes of the human papilloma virus (HPV) type 16, which function to dysregulate cell growth. HPV is a site specific DNA virus that is known to infect the basal cell layers and replicate during epithelial cell differentiation [Woodworth CD, et al. Characterization of normal human exocervical epithelial cells immortalized in vitro by papillomavirus types 16 and 18 DNA. Cancer Res. 1988 Aug 15;48(16):4620–8; Pecoraro G, et al. Differential effects of human papilloma virus type 6, 16, and 18 DNAs on immortalization and transformation. Proc Natl Acad Sci USA. 1989 Jan; 86(2): 563–7; Band V, et al. Human papilloma virus DNAs immortalize normal human mammary epithelial cells and reduce their growth factor requirements. Proc Natl Acad Sci U S A. 1990 Jan;87(1):463–7; Durst M, et al. Inverse relationship between human papillomavirus type 16 early gene expression and cell differentiation in nude mouse epithelial cysts and tumors induced by HPV-positive human cell lines. J Virol 1991 Feb;65(2):796–804; Merrick DT, et al. Altered expression of proliferation and differentiation markers in human papillomavirus 16 and 18 immortalized epithelial cells grown in organotypic culture. Am J Pathol. 1992 Jan;140(1):167–77; Pirisi L, et al. Continuous cell lines with altered growth and differentiation properties originate after transfection of human keratinocytes with human papillomavirus type 16 DNA. Carcinogenesis. 1988 Sep;9 (9):1573–9; Willey J C, et al. Immortalization of normal human bronchial epithelial cells by human papillomaviruses 16 or 18. Cancer Res. 1991 Oct 1;51(19):5370–7; Woodworth C D, et al. Human cervical and foreskin epithelial cells immortalized by human papillomavirus DNAs exhibit dysplastic differentiation in vivo. Cancer Res 1990 Jun 15;50(12):3709–15; and Blanton R A, Perez-Reyes N, Merrick D T, McDougall J K. Epithelial cells immortalized by human papillomaviruses have premalignant characteristics in organotypic culture. Am J Pathol. 1991 Mar;138(3):673–85]. More than 80 different types of human papilloma viruses (HPVS) have now been isolated from a variety of squamous epithelial lesions, and approximately 18 of them have been associated with anogenital tract lesions. Some of these, such as HPV type 6 (HPV-6) and HPV-11, are generally associated with benign proliferative lesions, including condyloma acuminata, which only infrequently progress to cancers. Others, such as HPV-16, HPV-18, HPV-31, HPV-33, and HPV-35, are associated with genital tract lesions, which are at risk for malignant progression, and with genital tract cancers [Ostrow R S, et al. A survey of human cancers for human papillomavirus DNA by filter hybridization. Cancer. 1987 Feb 1;59(3):429–34; and Turek L P, et al. The genetic program of genital human papillomaviruses in infection and cancer. Obstet Gynecol Clin North Am 1996 Dec;23(4):735–58].

Introduction of HPV 16 DNA into cells results in the immortalization of the cells at a high frequency and is independent of the genetic characteristics of the host cells [Woodworth C D, et al. (1988); Pecoraro G, et al.; Band, V., et al.; Durst M, et al.; Merrick D T, et al.; Pirisi L, et al.; Willey J C, et al.; Woodworth C D, et al. (1990); and Blanton R A, et al.]. Immortalization of human cells by HPV DNA is usually associated with aneuploidy and rearrangement of chromosomes [Oda D, et al. Chromosomal abnormalities in HPV-16-immortalized oral epithelial cells. Carcinogenesis 1996 Sep;17(9):2003–8; Hietanen S, et al. Isolation of two keratinocyte cell lines derived from HPV-positive dysplastic vaginal lesions. Int J Cancer 1992 Sep 30;52(3):391–8; Hashida T, et al. Induction of chromosome abnormalities in mouse and human epidermal keratinocytes by the human papillomavirus type 16 E7 oncogene. J Gen Virol 1991 Jul;72(Pt 7):1569–77; Smith P P, et al. Cytogenetic analysis of eight human papillomavirus immortalized human keratinocyte cell lines. Int J Cancer 1989 Dec 15;44(6):1124–31; and Klemi P J, et al. Association of DNA aneuploidy with human papillomavirus-induced malignant transformation of sinonasal transitional papillomas. Otolaryngol Head Neck Surg 1989 Jun;100(6):563–7]. Only those cells with integrated copies of HPV DNA become permanent lines, suggesting that genetic alterations caused by viral DNA integration and expression are necessary for continuous growth. HPV-16 or HPV-18 DNA has been found integrated in a high percentage of cervical carcinomas and in cell lines derived from these cancers. This is in contrast with the premalignant dysplastic lesions associated with HPV-16 and HPV-18, in which the viral DNA is usually found in an extrachromosomal state.

In several cases in which the number of integrated viral genomes was low enough to permit a detailed analysis, the integration pattern revealed remarkable specificity with respect to the circular viral genome [Yokoyama M, et al. Alterations in physical state and expression of human papillomavirus type 18 DNA following crisis and establishment of immortalized ectocervical cells. Virus Res 1995 Jul;37 (2):139–51; Gilles C, et al. Viral integration sites in human papilloma virus-33-immortalized cervical keratinocyte cell lines. Cancer Genet Cytogenet 1996 Aug;90(1):63–9; Fontijn R, et al. Maintenance of vascular endothelial cell-specific properties after immortalization with an amphotrophic replication-deficient retrovirus containing human papilloma virus 16 E6/E7 DNA. Exp Cell Res 1995 Jan;216(1):199–207; and DiPaolo J A, et al. Cellular and molecular alterations in human epithelial cells transformed by recombinant human papillomavirus DNA. Crit Rev Oncog 1993;4(4):337–60]. Integration occurs in the E1–E2 region, disrupting the E2 viral transcriptional regulatory circuitry. The E2 open reading frame (ORF), as originally demonstrated with the bovine papillomavirus type 1, encodes both positive- and negative-acting transcriptional regulatory factors. For HPV-16 and HPV-18, E2 appears to act principally as a repressor of the promoter from which the E6 and E7 genes are transcribed [Demeret C, et al. Different mechanisms contribute to the E2-mediated transcriptional repression of human papillomavirus type 18 viral oncogenes. J Virol 1997 Dec;71(12):9343–9; Rapp B, et al. Cell-type-specific separate regulation of the E6 and E7 promoters of human papillomavirus type 6a by the viral transcription factor E2. J Virol 1997 Sep;71(9):6956–66; Dowhanick J J, et al. Suppression of cellular proliferation by the papillomavirus E2 protein. J Virol 1995 Dec;69(12):7791–9; Thierry F, et al. Functional analysis of E2-mediated repression of the HPV18 P105 promoter. New Biol 1991 Jan;3(1):90–100.; Bernard B A, et al. The human papillomavirus type 18 (HPV18) E2 gene product is a repressor of the HPV18 regulatory region in human keratinocytes. J Virol 1989 Oct;63(10):4317–24; Goodwin E C, et al. Transactivation-competent bovine papillomavirus E2 protein is specifically required for efficient repression of human papillomavirus oncogene expression and for acute growth inhibition of cervical carcinoma cell lines. J Virol 1998 May;72(5):3925–34 and Ruley H E. Adenovirus early region 1A enables viral and cellular transforming genes to transform primary cells in culture. Nature 1983 Aug 18–24;304(5927):602–6]. The HPV genomes in cervical carcinomas and in derived cell lines are transcriptionally active, and the patterns of viral mRNA species are specific, with regular expression of the E6 and E7 ORFs.

The E7 ORF of HPV-16 encodes a 21-kilodalton phosphoprotein, and the E7 genes of HPV-16 and HPV-18 are sufficient for focus formation of established rodent fibroblasts such as NIH 3T3 cells. The E7 protein is functionally and structurally related to the adenovirus E1A proteins (AdE1A); it can transactivate the AdE2 promoter and can cooperate with an activated ras oncogene to transform primary rat cells. The amino-terminal 38 amino acids of E7 are strikingly similar to portions of conserved domain 1 (amino acids 37 to 49) and domain 2 (amino acids 116 to 137) of the AdE1A proteins as well as to portions of the large tumor antigens (T) of papovaviruses. The AdE1A, simian virus 40 (SV40) T, and HPV-16 E7 proteins form specific complexes with the product of the retinoblastoma tumor suppressor gene (p105-RB), and complex formation with p105-RB is mediated through these conserved sequences for AdE1A and SV40 T as well as for HPV-16 E7.

The transforming potential of the E6 gene has been less well defined [Villa L L, et al. Differences in transformation activity between HPV-18 and HPV-16 map to the viral LCR-E6-E7 region. Virology 1991 Mar;181(1): 374–7; Wilson S E, et al. Expression of E6/E7 or SV40 large T antigen-coding oncogenes in human corneal endothelial cells indicates regulated high-proliferative capacity. Invest Ophthalmol Vis Sci 1995 Jan;36(1):32–40; Halbert C L, et al. The E7 gene of human papillomavirus type 16 is sufficient for immortalization of human epithelial cells. J Virol 1991 Jan;65(1):473–8; and Barbosa M S, et al. In vitro biological activities of the E6 and E7 genes vary among human papillomaviruses of different oncogenic potential. J Virol. 1991 Jan;65(1):292–8]. In NIH 3T3 fibroblasts, it may contribute to characteristics of the transformed phenotype such as anchorage independence or tumorigenicity in nude mice. In human cells, E6 appears to cooperate with the E7 oncoprotein in mediating-cellular immortalization. Recently, it has been demonstrated that E6 binds to, and mediates the degradation of, the cellular tumor suppressor protein p53 [Band V, et al. Loss of p53 protein in human papillomavirus type 16 E6-immortalized human mammary epithelial cells. J Virol. 1991 Dec;65(12):6671–6].

It has been shown recently that both the E6 and E7 ORFs are necessary for the extension of the life span of human diploid fibroblasts. Mutation studies of the early HPV-16 genes that directly participate in the in vitro transformation of primary human keratinocytes have shown that both the full-length E6 and E7 genes are required for induction of keratinocyte immortalization and resistance to terminal differentiation. Keratinocyte transformation with HPV-18 DNA requires only the HPV-18 regulatory region and the E6/E7 genes which induce two progressive steps in cellular transformation [Hudson J B, et al. Immortalization and altered differentiation of human keratinocytes in vitro by the E6 and E7 open reading frames of human papillomavirus type 18. J Virol 1990 Feb;64(2):519–2; Munger K, et al. The E6 and E7 genes of the human papillomavirus Type 16 together are necessary and sufficient for transformation of primary human keratinocytes, vol. 63, No. 10, Journal of Virology, Oct. 1989, pp. 4417–4421; and Barbosa M S, et al. The E6 and E7 genes of HPV-18 are sufficient for inducing two-stage in vitro transformation of human keratinocytes,. Oncogene 1989 Dec;4(12):1529–32].

There is a need for cell lines derived from normal human middle ear epithelium which can be used, in turn, to study the molecular mechanisms involved in the pathogenesis that results in hearing loss. Furthermore, once derived, such cell lines can be used for a variety of purposes, including drug discovery, toxicity assays, discovery of novel genes important for middle ear epithelial cell function, tissue engineering and bionic device development.

SUMMARY OF THE INVENTION

The present invention is directed to a method of immortalizing middle ear epithelial cells that satisfies the need for cell lines derived from normal human middle ear epithelium, which can be used for in vitro assays to determine the molecular mechanisms involved in the pathogenesis of hearing disorders, including otitis media.

One version of the invention is a method for producing a non-tumorigenic immortalized cell line that retains phenotypic properties of middle ear epithelial cells. The first step of the method is providing a primary cell culture of human middle ear epithelial cells. The next step is introducing a polynucleotide encoding an exogenous immortalizing gene into the middle ear epithelial cells. The last step is selecting for immortalized cells that express the exogeous immortalizing gene and retain phenotypic properties of middle ear epithelial cells. The polynucleotide is typically a subgenomic fragment of a virus, such as SV40, adenovirus, and human papilloma virus. Preferably, the immortalizing gene is the E6 and E7 genes of said human papilloma virus types 16, 18, 31, 33, or 35, with type 16 being most preferred. The polynucleotide is typically contained in a viral or plasmid vector, such as a retrovirus, adenovirus, or adeno-associated virus vector, most preferably a replication-defective retrovirus construct.

Another version of the invention is a substantially pure cell line of immortalized non-tumorigenic human middle ear epithelial cells, which expresses an exogenous immortalizing gene, such as SV40 T antigen, adenovirus E1A, or human papilloma virus E6 and E7 genes. Preferably the immortalizing gene is the E6 and E7 genes of human papilloma virus types 16, 18, 31, 33, and 35, with type 16 being most preferred.

In another version of the present invention, the substantially pure cell line of immortalized human middle ear epithelial cells actively expresses the E6 and E7 gene of human papilloma virus 16, wherein the immortalized cell line maintains phenotypic characteristics of human middle ear epithelial cells, such as immunostaining positive of for cytokeratins 4, 7, and 18, but not desmin, vimentin, and Factor VIII. The cells do not have a neoplastic phenotype and exhibit contact inhibition and anchorage dependence.

A most preferred version of the present invention is a cell line having the identifying characteristics of ATCC Accession # CRL PTA-81.

Another version of the present invention is a method for determining the effect of a pharmacological agent on cells of the middle ear. The first step of the method is contacting the immortalized middle ear epithelial cell line with a pharmacological agent and then determining the effect of the pharmacological agent on the cell line. The effect can be a change in cell growth, a change in a phenotypic characteristic of the cell line, or an increase or decrease in expression of a cellular gene. The effected cellular genes can be mucins, cytokines, growth factors and molecules of innate immunity, including, but not limited to, defensins, surfactant proteins, lysozyme, and lactoferrin. Moreover, the pharmacological agent can belong to a family such as chemicals, drugs, hormones, cytokines, and growth factors.

The present invention also provides a kit for screening a pharmacological agent on middle ear epithelial cells, which includes a container of the immortalized middle ear epithelial cells described above.

BRIEF DESCRIPTION OF THE DRAWINGS

These and other features, aspects, and advantages of the present invention will become better understood with regard to the following description, appended claims, and accompanying drawings, where:

FIG. 1 demonstrates "dome" formation by both primary human middle ear epithelial cells (a) and by the HPV-transformed human middle ear epithelial cell line HMEEC-1(b);

FIG. 2 demonstrates the growth rate of both primary human middle ear epithelial cells (open diamonds) and that of the HPV-transformed human middle ear epithelial cell line, HMEEC-1 (closed squares);

FIG. 3 demonstrates the senescence and/or death of primary human middle ear epithelial cells (Primary cells) in basal media with or without growth additives such as EGF, insulin and BPE compared with the survival and growth of HPV-transformed human middle ear epithelial cell line HMEEC-1 even in basal media;

FIG. 4 demonstrates the staining of both primary cultures and the HMEEC-1 cells by cytokeratin (a and b) but not vimentin (c and d) antibodies;

FIG. 12 demonstrates the karyotype analysis of the HMEEC-1 at passage 20; and

FIG. 13 demonstrates punctate expression of the tight junction protein ZO-1 by a second clone of the HPV-transformed human middle ear epithelial cell line, HMEEC-2.

DETAILED DESCRIPTION OF THE INVENTION

Figure 5:
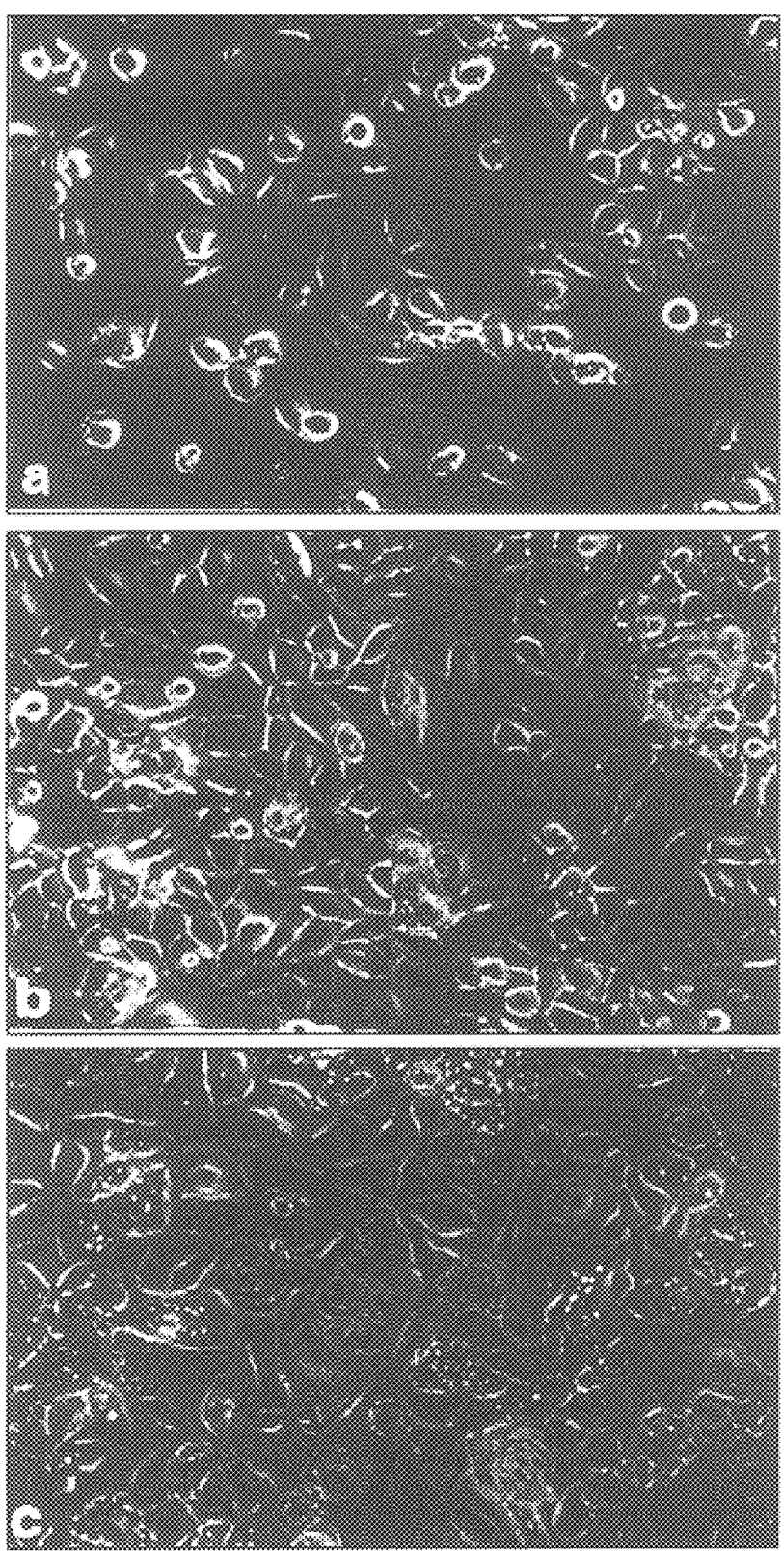
FIG. 5 demonstrates the resistance of HPV-transformed human middle ear epithelial cell line, HMEEC-1 at 0, 2, and 7 days after G418 addition (panels, a, b and c, respectively)

The present invention is directed to a novel immortalized human middle ear epithelial cell line that retains phenotypic properties of human middle ear epithelial cells. The present invention is also directed a method of immortalizing middle ear epithelial cells by introducing an exogenous immortalizing gene into cells of a primary culture and selecting for immortalized cells expressing the exogenous gene. The present invention is also directed to methods of using the immortalized human middle ear epithelial cells in screening assays.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are described herein. The publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

A full description of the method for immortalization and selection, as well as the properties of the immortalized cell line is given in the following sections.

I. Primary cultures

The first step of the method for immortalizing human middle ear epithelial cells is providing a primary cell culture of human middle ear epithelial cells. A detailed description of methods for establishing primary cell cultures from explants of human middle ear epithelium obtained from human subjects is provided in Example 1 of the present disclosure.

II. Immortalization

The second step of the method for immortalizing human middle ear epithelial cells is introducing a polynucleotide encoding an exogenous immortalizing gene into the middle ear epithelial cells of the primary culture.

A. Exogenous immortalizing genes

A number of viral genes, such as the SV40 T antigen, adenovirus E1A, and human papilloma virus E6 and E7 genes are known in the art for their ability to transform primary cell cultures into continuous cell lines. Thus an exogenous immortalizing gene according to the present invention is typically a polynucleotide, which is a subgenomic fragment of a virus, such as SV40, adenovirus, or human papilloma virus. Preferably the immortalizing gene is a subgenomic fragment of a human papillomavirus encoding the E6 and/or E7 gene of human papilloma virus types 16, 18, 31, 33 or 35, with type 16 being most preferred.

B. Vectors

To facilitate the introduction and expression of the exogenous immortalizing gene, the polynucleotide encoding the immortalizing gene is typically contained in a viral or plasmid vector. The viral or plasmid vector can selected from a variety of mammalian expression vectors known in the art, such retrovirus, adenovirus, and adeno-associated virus vectors. Preferably, the vector is a replication-defective retrovirus construct.

An exemplary retrovirus vector is pLXSN (GenBank Accession # M28248), which is available commercially (Clontech). The vector contains 5' and 3' LTRs and a psi+ packaging signal derived from Moloney murine leukemia virus (MoMuLV). The retroviral promoter, i.e., the 5' viral LTR, controls expression of the exogenous immortalizing gene, which is inserted into a multiple cloning site. An SV40 early promoter controls expression of a neomycin resistance gene, Neo$^r$, which allows antibiotic selection of eukaryotic cells in G418. The pLXSN vector also includes the pBR322 origin of replication and *E. coli* Amp$^r$ gene for propagation and antibiotic selection of DNA plasmids in bacteria.

Upon transfection of the DNA plasmid into a suitable packaging cell line, pLXSN can express a transcript containing the LTRs, a viral packaging signal, the immortalizing gene insert, and a selectable marker. However it does not contain the gag, pol, and env genes needed for particle formation and replication. These genes are stably integrated into packaging cell lines, such as PT67 (Clontech) or PA317 (ATTC CRL 9078). Once in the packaging cell, the RNA transcript from the vector is packaged into infectious, replication incompetent retroviral particles. These retroviral particles can infect target cells and transmit the exogenous immortalizing gene along with the selectable marker, but cannot replicate since they do not contain the viral genes that are essential for replication.

C. Methods for introducing polynucleotide/vector into cells

A variety of standard methods are known in the art for introducing the exogenous immortalizing gene into the immmortalized cells of the present invention. These include transfection (precipitation and uptake of exogenous DNA with calcium salts), electroporation, lipofection, and transduction. A preferred transduction procedure utilizing a defective retrovirus construct is described in Example 2 of the present disclosure.

III. Selection

The third step of the method for immortalizing human middle ear epithelial cells is selecting for immortalized cells that express the exogeous immortalizing gene and retain phenotypic properties of middle ear epithelial cells.

A. Selectable markers/G418 resistance

Figure 6:
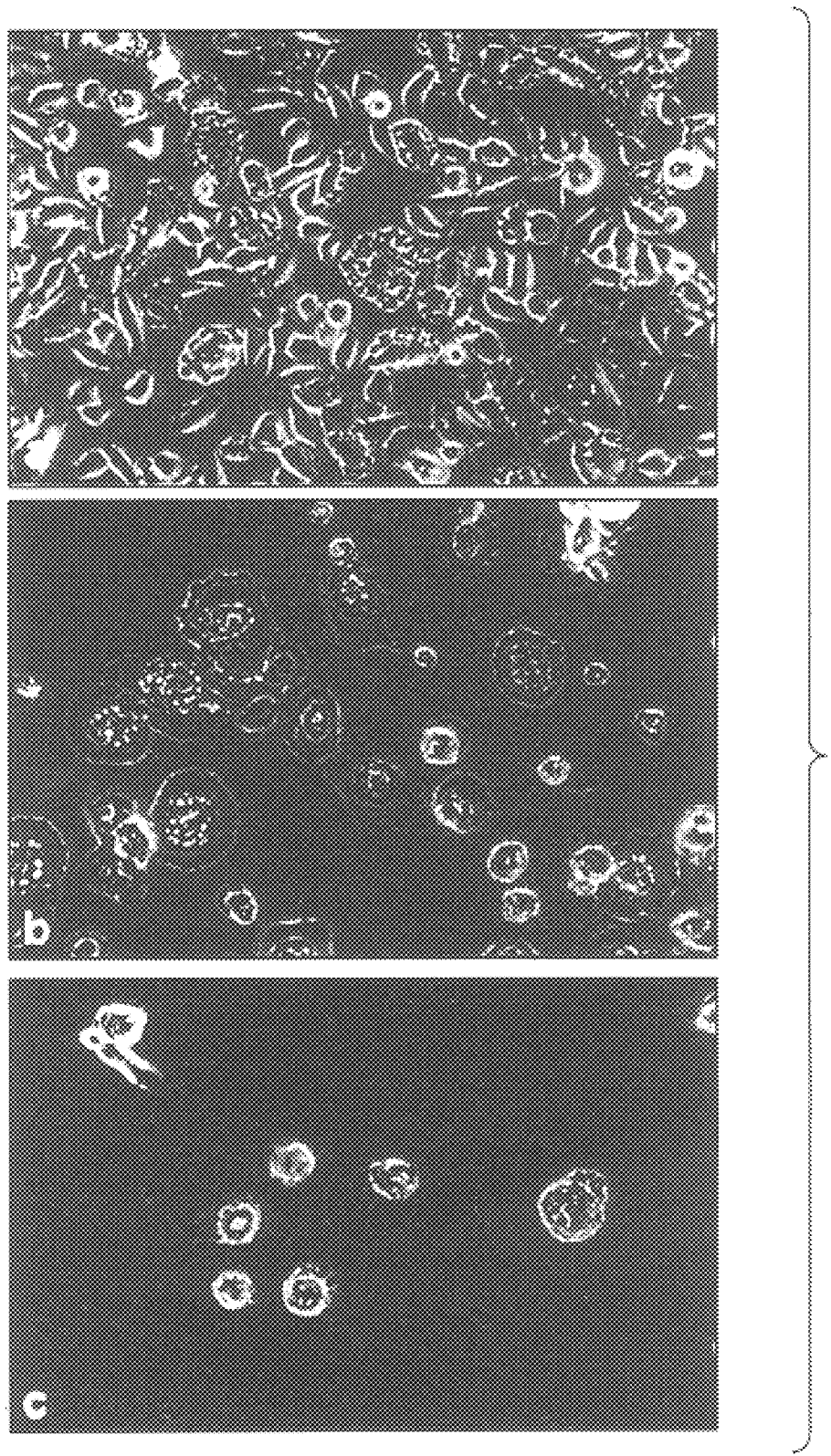
FIG. 6 demonstrates the sensitivity of primary human middle ear epithelial cells at 0, 2, and 7 days after G418 addition (panels, a, b and c, respectively)

A preliminary selection procedure for cells that have incorporated an exogenous immortalizing gene can be conducted when using a vector that includes a selectable marker, such as $Neo^r$. As shown in FIG. 5 and 6, immortalized cells become resistant, whereas primary cells remain sensitive to the presence of G418 in the culture media.

B. Senescence

Primary cells generally undergo senescence after about 5–6 passages. In contrast, the immortalized cells of the present invention continue to proliferate after repeated passage, e.g. more than 30 passages.

C. Expression of immortalizing genes

Figure 7:
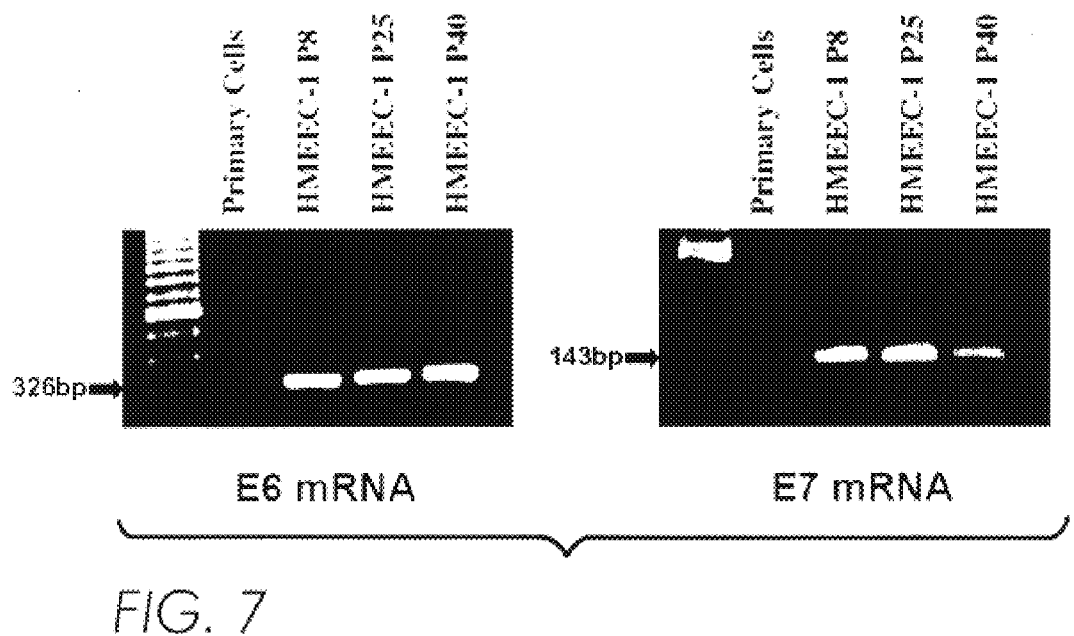
FIG. 7 demonstrates the expression of HPV-16 E6 and E7 gene sequences, using reverse transcription followed by polymerase chain reaction (RT-PCR) of RNA from the HMEEC-1 at passage 8 (HMEEC-1 P8), passage (HMEEC-1 P25), and at passage 40 (HMEEC-1 P40)

While G418 resistance and high passage numbers are indirect methods for selecting cells that express an exogenous immortalizing genes, more direct methods for detecting DNA or mRNA encoding exogenous gene sequences, e.g., hybridization or nucleic acid amplification assays, can also be used to show the presence of exogeous gene sequences in the immortalized middle ear epithelial cells of the present invention. For example, FIG. 7 shows the detection of HPV-16 E6 and E7 gene sequences in HMEEC-1 using reverse transcription followed by polymerase chain reaction of RNA from the immortalized cells.

IV. Phenotypic Characteristics

The immortalized middle ear epithelial cells of the present invention retain many of the phenotypic characteristics of the primary cells from which they were derived. The growth properties, tumorigenicities, cytogenetics and intermediate filament profiles of this immortalized human middle ear epithelial cell were characterized. Comparative studies with normal human middle ear epithelial cells show that the immortalized cells have retained several differentiated properties of normal middle ear epithelial cells and may be useful as model for studying normal cell biology of human middle ear epithelial cells and the molecular pathogenesis of otitis media.

A. Morphology

The immortalized cells of the present invention typically retain the morphology of the normal middle ear epithelial cells from which they were derived. For example, FIG. 1 shows "dome" formation by both normal human middle ear epithelial cells (a) and by the HPV-transformed human middle ear epithelial cell line HMEEC-1 (b).

B. Growth in basal media

As shown in FIG. 3, immortalized cells of the present invention are able to grow in basal media with or without growth additives such as EGF, insulin and BPE. Accordingly, these cells are particularly useful for identification and purification of growth factors important for growth and differentiation of human middle ear epithelial cells. Responses to growth factors can be studied in precisely defined growth media and any factors produced by the cells may be identified and purified in the absence of serum.

C. Epithelial cell markers

The immortalized cells continue to express several epithelial cell markers, which can be detected by immunohistochemical staining (see, e.g., FIG. 4). The immortalized middle ear epithelial cells of the present invention typically stain positive for cytokeratins 4, 7, and 18. Moreover, vimentin and desmin, proteins expressed in cells of mesenchymal origin, such as fibroblasts, are not detected. Furthermore, Factor VIII expression is not detected, which indicates the cells are not of endothelial origin.

D. Absence of neoplastic phenotype

Although the immortalized cells of the present invention are capable of continuous proliferation, they do not acquire a neoplastic phenotype. The cells are non-tumorigenic, as shown by the failure of tumors to develop after subcutaneous injections of the immortalized cells in nude mice (see Example 10 for further details). Moreover the immortalized cells exhibit contact inhibition and anchorage dependence (see, e.g., Example 8).

V. Methods of Use

The immortalized cells of the present invention retain several differentiated properties of normal middle ear epithelial cells. Accordingly the immortalized cells can be a useful model for studying the normal cell biology of human middle ear epithelial cells as well the molecular pathogenesis of otitis media. For example, restoring the normal regulation of cytokines can prevent the inflammatory process of otitis media from escalating to pathological levels. Furthermore, regulating the expression of pathologically relevant genes such as the mucins, aquaporins or surfactant proteins will decrease mucus build up and thus ameliorate the severity of otitis media. Regulation of these genes may also reduce middle ear effusion product and improve Eustachian tube function. Therefore, an objective of the present invention is to provide a cell line for screening all families of pharmacological agents that may, directly or indirectly, prevent or decrease the morbidity of otitis media and its sequelae.

A. Screening Assays

In particular, the cell line can be used in methods for determining the effect of a pharmacological agent on cells of the middle ear. As an initial step, the immortalized cells are grown in vitro in medium containing the pharmacological agent and then, after a suitable period, determining whether the pharmacological agent had an effect. The pharmacological agents can include chemicals, drugs, hormones, cytokines, and growth factors.

B. Growth and Toxicity Assays

The toxicity and growth inhibiting or enhancing properties of the pharmacological agent can be determined by measuring the extent of cell death (e.g., trypan blue exclusion assay) or by growth assays (e.g., Examples 4 and 5).

C. Differential Gene Expression

Alternatively, the effect of the pharmacological agent may consist of a change in a phenotypic characteristic of the cell line, such as an increase or decrease in expression of a cellular gene.

An antibody or nucleic acid probe specific for genes expressed in middle ear cells, may be used to detect the presence of the respective protein (using antibody) or polynucleotide (using nucleic acid probe) in the immortalized cell.

The antibody and nucleic acid probes are generally detectably labeled, for example, with a radioisotope, a fluorescent compound, a bioluminescent compound, a chemiluminescent compound, a metal chelator or an enzyme. When proteins are to be detected, immunoassays and immunohistochemical assays may be used. A technique which may result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Another method for detecting polynucleotides is to amplify the nucleic acid using sequence specific primers. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used. Those of ordinary skill in the art will know or will be able to ascertain, using routine experimentation, the suitable labels and assay formats to use.

Accordingly, the immortalized cells can be used for the analysis of differential gene expression and also for the study of the regulation of pathologically relevant genes such as mucins, aquaporins, cytokines, growth factors, defensins, surfactant proteins, lysozyme, and lactoferrin. Moreover, these gene products can be assayed for activities, such as cell-microbe interaction, role in intracellular signaling, role in production of mucus and other biological secretions and other intra and extracellular events that may be targeted by pharmaceutical agents in order combat otitis media infection and its sequelae.

Figure 8:
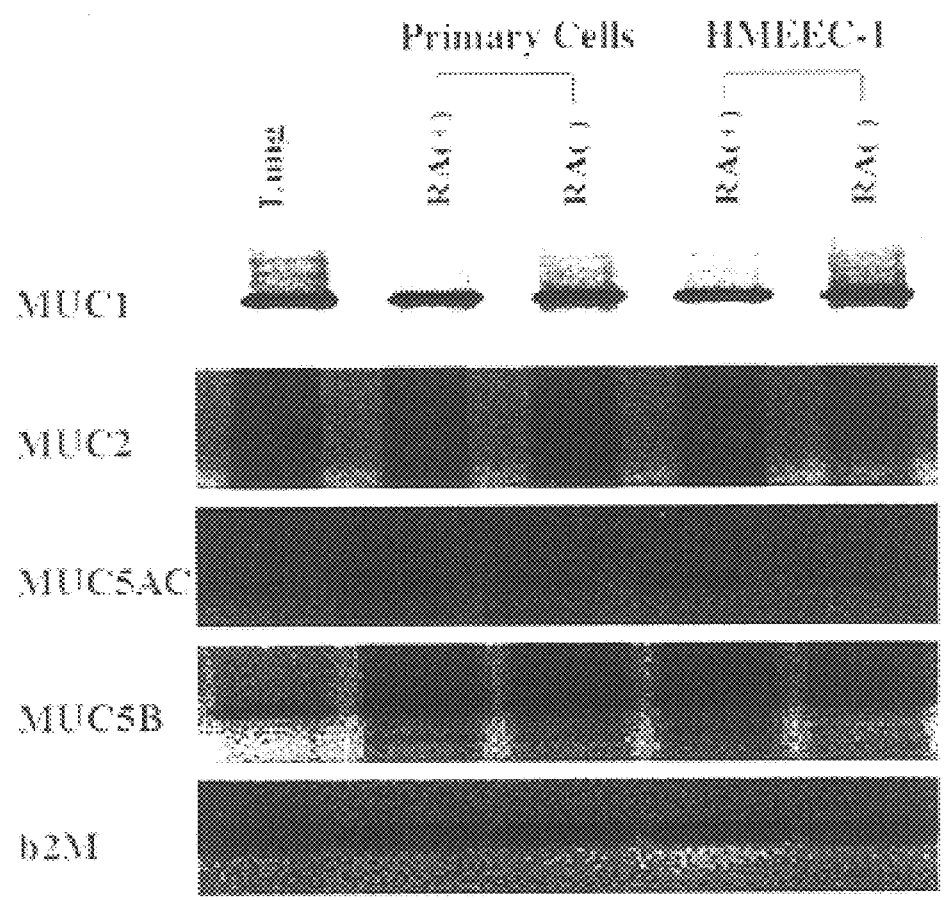
FIG. 8 demonstrates, by RT-PCR, the effect of retinoic acid (RA) on mRNA expression of mucin genes MUC1, MUC2, MUC5AC, and MUC5B in both primary human middle ear epithelial cells (Primary cells) and in the HPV-transformed human middle ear epithelial cell line HMEEC-1.

In one embodiment of the present invention, shown in FIG. 8, the expression of mucin genes is detected by reverse transcription (RT) of cellular mRNA followed by polymerase chain reaction (PCR) amplification of the transcripts. FIG. 8 further demonstrates the effect of a pharmacological agent, namely retinoic acid, which upregulates MUC2 and MUC5AC, but not MUC1 or MUC5B mRNA levels in the immortalized cells.

Figure 9:
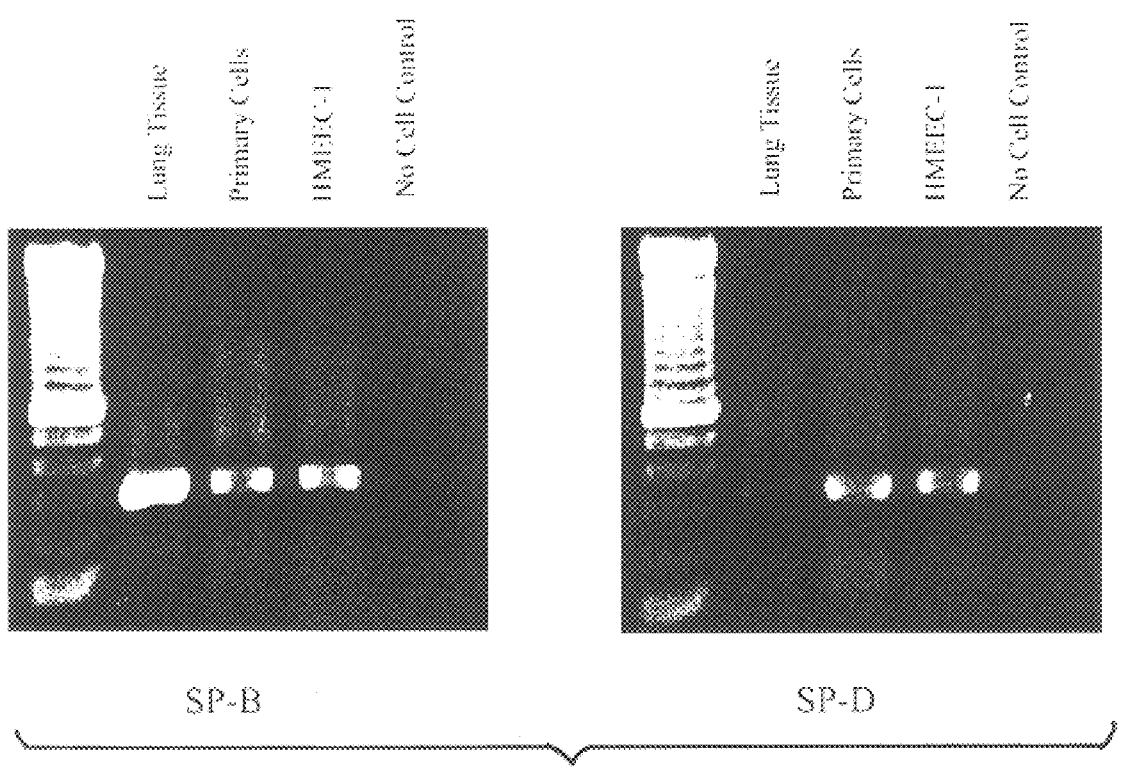
FIG. 9 demonstrates by RT-PCR that mRNAs for surfactant proteins B and D (SP-B and SP-D) are expressed in both primary human middle ear pithelial cells and in the HPV-transformed human middle ear epithelial cell line HMEEC-1.

In another embodiment of the present invention expression of mRNAs for surfactant proteins B and D (SP-B and SP-D) in immortalized and normal cells is detected by RT-PCR (see FIG. 9).

In yet another embodiment RT-PCR detects mRNAs for the Beta Defensins 1 and 2 (HBD-1 and HBD-2), which are expressed in both primary human middle ear epithelial cells and in the HPV-transformed human middle ear epithelial cell line HMEEC-1.

Figure 11:
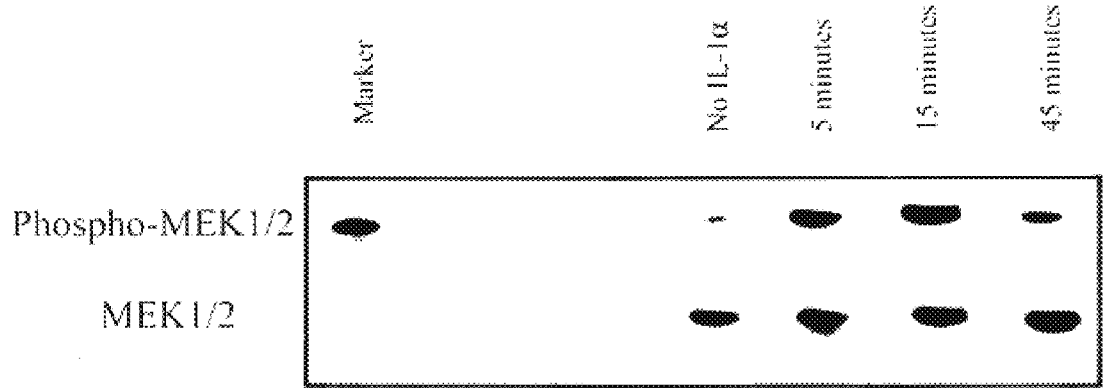
FIG. 11 demonstrates, using antibodies specific to the phosphorylated (phospho-MEK1/2) and unphosphorylated (MEK1/2) MEK protein, that treatment of HMEEC-1 cells with IL-1 alpha for 5, 15 and 45 minutes activates MEK1/2 (MAPK kinase)

The embodiment illustrated in FIG. 11 shows the cytokine, IL-1 alpha, activates MEK1/2 (MAPK kinase) in HMEEC-1 by using an immunological detection method that distinguishes between the phosphorylated and unphosphorylated forms of the protein.

D. Further applications of the present invention

The cell line can be used for discovery of new genes as targets for therapy. Several methods of differential gene expression are currently available and in use.

In one method, large numbers of human complementary DNAs (cDNAs) can be printed on glass with high-speed robotics to yield microarrays. These DNA "chips" can then be used to quantitatively monitor differential expression human genes using a highly sensitive two-color hybridization assay. For such experiments, the cells are treated under two different conditions, RNA is extracted and differentially labeled using two fluorescent dye (one corresponding to each condition). Differential expression measurements of the genes on the chips can then be made by means of simultaneous, two-color fluorescence hybridization [Schena M, et al. Parallel human genome analysis: microarray-based expression monitoring of 1000 genes. Proc Natl Acad Sci USA 1996 Oct 1;93(20):10614–9; Schena M, et al. Quantitative monitoring of gene expression patterns with a complementary DNA microarray. Science 1995 Oct 20;270 (5235):467–70].

Another powerful method, called serial analysis of gene expression (SAGE), allows the quantitative and simultaneous analysis of a large number of transcripts. It is based on isolating concatenating, cloning and sequencing, short diagnostic sequence tags from tissues or differentially treated cells. Sequencing of as few as 1000 tags provides a characteristic gene expression pattern, although the usual number of tags analyzed is 50,000. SAGE is a broadly applicable approach to the quantitative cataloging and comparison of expressed genes in a variety of normal, developmental, and disease states [Velculescu V E, et al. Serial analysis of gene expression. Science 1995 Oct 20;270(5235):484–7].

Yet another widely used method for the analysis of differential gene expression is representational difference analysis (RDA). RDA is an efficient PCR-based subtraction approach for finding the differences between complex genomes or expressed sequences and has been applied to numerous issues including the cloning of probes for the detection of genetic lesions in cancer, the identification of sequences from the genomes of unknown pathogens and the rapid isolation of polymorphic markers linked to a trait without the use of pre-existing genetic maps.

The cDNA RDA technique can be used to identify genes responsible for cellular response to particular stimuli [Lisitsyn N A. Representational difference analysis: finding the differences between genomes. Trends Genet 1995 Aug;11(8):303–7; Lerner A, et al. Cross-linking of T-cell receptors on double-positive thymocytes induces a cytokine-mediated stromal activation process linked to cell death. *EMBO J* 1996 Nov 1;15(21):5876–87; and Gruidl M, et al. The progressive rise in the expression of alpha crystallin B chain in human endometrium is initiated during the implantation window: modulation of gene expression by steroid hormones. Mol Hum Reprod 1997 Apr;3(4):333–42]. For example cDNA from lipopolysaccharide (LPS)-stimulated cells can be subtracted from cDNA made from untreated cells. This subtracted library can then be cloned and a number of randomly picked clones can be sequenced. Alternatively, the fragments can be cloned into a plasmid vector and sequenced. This approach has been successfully used to identify genes encoding cytoskeletal components as well as those involved in DNA replication, metabolism, signal transduction, transcription, translation and transport, amongst others.

Many of the genes thus identified can then assessed as targets of potential therapeutics [Chu CC, et al. Expressed genes in interleukin-4 treated B cells identified by cDNA representational difference analysis. Mol Immunol 1998 Jun;35(8):487–502]. Furthermore, cDNA-RDA and arrayed filters or microarrays (gene chips) can be combined to yield a powerful method for high-throughput gene expression difference analysis [Chang D D, et al. Characterization of transformation related genes in oral cancer cells. Oncogene 1998 Apr 16;16(15):1921–30].

The immortalized cells will also be capable of producing large quantities of gene products without the need to replace senescent cell lines. Should therapeutic genes and/or proteins that decrease the occurrence or duration of otitis media be found, the cells can be engineered to express such molecules and be used as therapeutic implants. In such a case the cells would contain and express the exogenous genes that may include genes that may correct a gene defect responsible for susceptibility to otitis media.

EXAMPLES

Materials and Methods

Various materials were obtained from the sources indicated below. Flasks (Costar); Media, Buffers, Trypsin (Bio-Whittaker, San Diego, Calif.), G418 (Gibco-BRL, Gaithersburg, Md.); Fetal Bovine Serum (GIBCO BRL-Life Technologies, Inc. Gaithersburg, Md.); Restriction enzymes (New England Biolabs, Beverly, Mass.); Type I rat tail collagen (Collaborative Biochemical Products, Bedford, Mass.).

Example 1
Primary cell cultures

Primary cultures of normal human middle ear epithelial cells (HMEC) were established from explants of fresh human middle ear epithelium obtained from patients undergoing neuro-otologic surgery for acoustic neuromas. Pieces of middle ear mucosa, measuring 3 mm×3 mm were removed from the region near the protymapanum. After washing twice in $Mg^{2+}$ and $Ca^{2+}$ free phosphate buffered saline (1×, pH 7.4), each piece of mucosa was cut with a scalpel into three 1 mm fragments. The fragments were then placed into 35-mm tissue culture dishes that had been pre-coated with type I rat tail collagen (Collaborative Biochemical Products, Bedford, Mass.).

The fragments were grown in serum-free, hormone and growth factor supplemented media (SFM-HG), containing penicillin (100 U/ml) and streptomycin (100 mg/ml). After 2–3 weeks, HMECs began to migrate out from the explants and formed a monolayer. The few contaminating fibroblasts were physically removed with a surgical scalpel under the microscope. Using this technique primary cultures were successfully established from five of seven donors.

For passage, the cells were dissociated with the HBSS containing 0.025% trypsin/0.01% EDTA (Bio-Whittaker, San Diego, Calif.) and split at a 1:4 ratio. The culture media was replaced twice a week.

Example 2
Immortalization

The PA317 amphotropic packaging cell line was used for the immortalization procedure. These cells have been stably transfected with a replication-defective retrovirus construct, pLXSN16E6–E7 (HPV-16 E6E). PA 317 cells were grown to 70–80% confluence, and supernatants were collected after 24 hours and stored in aliquots at −80° C.

Passage 3 human middle ear epithelial cell cultures (at 50–70% confluence) were infected with 1 ml of virus stock diluted in 9 ml of fresh SFM-HG for 48 hours. The virus was then removed and the medium was replaced with fresh SFM-HG. The cells were allowed to proliferate and once at 70% confluence, they were trypsinized and re-seeded in fresh SFM-HG medium containing G418 (Gibco-BRL, Gaithersburg, Mass.) at a concentration of 0.4 mg/ml.

FIG. 5 demonstrates the resistance of HPV-transformed human middle ear epithelial cell line, HMEEC-1 to G418. Cells were photographed prior to selection, at 2 days and at 7 days post G418 addition (panels, a, b and c, respectively). In contrast, FIG. 6 demonstrates the sensitivity of primary human middle ear epithelial cells to G418. Cells were photographed prior to selection, at 2 days and at 7 days post G418 addition (panels, a, b and c, respectively).

Cells were kept in the G418-containing selection media for 14 days. After the selection procedure, the culture media was changed to SFM-HG without G418 and the cells were expanded. At this stage, half of the culture was frozen and the other half was used for long-term propagation. To propagate the cells, the cultures were split at a ratio of 1:4 once a week. Cells that continued to proliferate after 30 passages, were considered to be immortalized.

Example 3
Cell Freezing

Pelleted cells were resuspended in SFM-HG containing 10% DMSO at a concentration of $1\times10^6$ cells/ml and subsequently aliquoted in 2 ml freezing tubes. The tubes were placed at −70° C. overnight and transferred to liquid nitrogen the next day.

Example 4
Colony Isolation Procedure

Flasks containing colonies were rinsed twice with HBSS and the colonies were marked from outside the flask. Cloning rings dabbed with autoclaved vacuum grease were then used to encircle the colonies. To dislodge the cells, HBSS containing 0.025% trypsin/0.01% EDTA was added to the inside of each cloning ring (enough to cover the colony) and the flask was incubated at 37° C. until the cells were dissociated. The cells were then counted and transferred to coated T25 flasks containing ml SFM-HG medium.

Example 4
Determination of cell growth

To compare the growth of the primary cultures and the transformed cells, approximately $7\times10^3$ cells/well were plated in a 24-well culture plate. The cells were counted every two days and the population doubling time (DT) was calculated using the following formula: DT=T/x, where T=total time elapsed and x=number of generations. LogN= $LogN_0$ +xLog2 where N=final number of cells, $N_0$=initial number of cells.

FIG. 2 shows the growth characteristics of both normal human middle ear epithelial cells (open diamonds) and that of the HPV-transformed human middle ear epithelial cell line HMEEC-1 (closed squares).

Example 5
Growth factor response

To measure the effect of various media on growth parameters, cells were cultured for at least two passages in the following three media: SFM-HG, BEGM, and BEGM plus EGF, Insulin and BPE. Approximately $2.5\times10^4$ cells/ well were plated in a 6-well culture plate. The number cells per well was determined every other day, for 14 days. The population doubling times were calculated as above.

FIG. 3 shows primary human middle ear epithelial cells (Normal HMEC) senesce and/or die in basal media with or without growth additives such as EGF, insulin and BPE. In contrast, the HPV-transformed human middle ear epithelial cell line HMEEC-1 survive and thrive, even in basal media.

Example 6
Morphologic studies

For light microscopy, immortalized middle ear epithelial cells were cultured on cover slips placed inside collagen-coated petri dishes. The cells were visualized and photographed using an inverted phase contrast microscope (Zeiss, Axiovert 135).

FIG. 1 shows "dome" formation by both normal human middle ear epithelial cells (a) and by the HPV-transformed human middle ear epithelial cell line HMEEC-1 (b).

Example 7

Immunohistochemistry

Cells were cultured on collagen I coated coverslips (BioCoat) for immunohistochemical staining. They were fixed with pre-chilled methanol (−20° C.) for minutes and permeabilized with acetone (4° C.) for 2 minutes and dried, then rinsed with PBS. The coverslips with cultured cells were incubated with 10% normal rat serum (Calbiochem, San Diego, Calif.) in PBS to block non-specific antigens for 1 hour.

Expression of cytokeratins, Factor VIII, vimentin and ZO-1 were assessed with using the respective antibodies. A comparison was done between the primary cultures and the immortalized cells. Anti-ZO-1 immunostaining was done by the same procedure as above. The cultured cells were also stained with mouse monoclonal anti-cytokeratin antibody C-11 (Sigma) and monoclonal anti-vimentin antibody VIM-13.2 (Sigma) to confirm the epithelial nature of the cell line. As a negative control, the slides were incubated with 5% normal mouse serum (Calbiochem) instead of mouse monoclonal antibodies for 1 hour. Excess antibody was rinsed off with PBS, after which the coverslips were covered with fluorescein isothiocyanate (FITC)-labeled goat anti-mouse IgG (Oncogene Science) and incubated for 1 hour at 37° C. After washing excess antibodies, the coverslips were mounted on slide glass in glycerin gel. Slides were examined with a light microscope equipped with incident-light fluorescence (Zeiss, Axiovert 135).

FIG. 4 shows immunofluorescent staining of both primary cultures and the HMEEC-1 cells by cytokeratin (a and b), but not vimentin (c and d) antibodies. ZO-1 staining is shown in FIG. 13. Although the HMEEC-1 line showed cytoplasmic labeling of ZO-1, a second clone, HMEEC-2, showed punctate staining of cell eripheries.

Example 8

Soft agar assay for anchorage independence

The soft agar used in the anchorage independence assay was prepared using Noble agar (Difco, Detroit, Mich.) in SFM-HG media. The base agar consisted of 0.9% agar, whereas the top agar contained 0.36% agar. For the assay, 2 ml of base agar was dispensed into 35 mm (2 mm grid) dishes and allowed to cool. The cell suspension containing $1 \times 10^4$ cells/ml, in 5 ml of 0.36% top, agar was then added to the plates. The plates were checked after 21 days and no colony larger than 0.125-mm diameter was counted.

Example 9

Karyotype analysis

A complete karyotype analysis was carried out by Dr. J. Kaplan and B. Hukku, Children's Hospital of Michigan, Detroit, Mich. FIG. 12 shows the karyotype analysis performed on the HMEEC-1 at passage 20. The results indicate that the cells are hypodiploid, possess a Y chromosome and have a chromosome counts in the range of 39–47. The average chromosome number for HMEEC-1 was 43 and the Y chromosome was present in about 40% of metaphases examined. Some of the autosomes appeared abnormal in appearance, suggesting the presence of gross deletions or translocations.

Example 10

Tumorigenecity in nude mice

To determine their tumorigenicity, the transformed cells were resuspended at a concentration $5 \times 10^7$ cell/ml in 0.2 ml of PBS. The cells were then injected subcutaneously into the backs of five-week-old BALB/c nu/nu athymic mice. Injection of 0.2 ml of PBS, without cells, served as the control. For a period of 6 months, the mice were examined weekly without evidence of tumor formation.

Example 11

RT-PCR

Polymerase chain reaction (PCR) assays were performed essentially following the package insert of the commercially available Gene-Amp kit (document No. 55635–6/89, available from Perkin-Elmer/Cetus, Emeryville, Calif.). The following reagents were mixed in a 0.5 mL polypropylene tube and used in performing PCR:

| Reagent | Final Concentration |
|---|---|
| Water | (to give final volume = 50 µl) |
| Reaction Buffer: | |
| | 10 mM TRIS pH 8.3 |
| | 50 mM KCl |
| | 1.5 mM MgCl |
| | 0.01% gelatin |
| dNTP mixture | 200 µM each of dATP, dCTP, dGTP, and TTP |
| PCR (Forward) | 1 µM |
| PCR (Reverse) | 1 µM |
| DNA | 10 µl 1 ng/100 µl |
| Amplitaq Gold DNA polymerase, 25 units/1 ml | |

After mixing, the reaction mixture was overlayed with a drop of mineral oil to 30 cycles of PCR, with the following cycle profile: 30 second denaturation, 1 minute annealing and 2 minute extension. The PCR products were run on a 1.2% TAE agarose gel.

Expression of various genes was confirmed using the following PCR primers specific for:

E6 and E7 genes of HPV:

E6(Forward) 5'-GCAAGCAACAGTTACTGCGACGT-3'(SEQ ID NO. 1)

E6(Reverse) 5'-GCAACAAGACATACATCGACCGG-3' (SEQ ID NO. 2)

E7(Forward) 5'-GATGGTCCAGCTGGACAAGC-3' (SEQ ID NO. 3)

E7(Reverse) 5'-GTGCCCATTAACAGGTCTTC-3' (SEQ ID NO. 4)

FIG. 7 demonstrates the integration of HPV-16 E6 and E7 gene sequences into the genome of HMEEC-1 cells. Reverse transcription, followed by polymerase chain eaction (RT-PCR) of RNA from the HMEEC-1 shows that the E6 and E7 sequences are stable and being actively transcribed at passage 8 (HMEEC-1 P8), passage 25 (HMEEC-1 P25), and at passage 40 (HMEEC-1 P40). In contrast, no RT-PCR products for either E6 or E7 are seen in the primary human middle ear epithelial cells, indicating that these cells do not have the HPV sequences.

Mucins (1,2, 5AC and 5B):

```
MUC1
(Forward)    5'-CTCCTTTCTTCCTGCTGCTG-3'      (SEQ ID NO. 5)
(Reverse)    5'-CAGCTGAACCTGAAGCTGGT-3'      (SEQ ID NO. 6)

MUC2
(Forward)    5'-TGC CTG GCC CTG TCT TTG-3'   (SEQ ID NO. 7)
(Reverse)    5'-CAG CTC CAG CAT GAG TGC-3'   (SEQ ID NO. 8)

MUC5AC
External
Primers
(Forward)    5'-GTCACCAACACCAGCAAGAG-3'      (SEQ ID NO. 9)
(Reverse)    5'-TCGAGCGAGTACATGGAAGA-3'      (SEQ ID NO. 10)

MUC5AC
Nested
Primers
(Forward)    5'-CCACTGTGTGACCCACCA-3'        (SEQ ID NO. 11)
(Reverse)    5'-TGCTGCTGGATGATCAGG-3'        (SEQ ID NO. 12)

MUC5B
(Forward)    5'-ATGAAACCTGGGTCAACAGC-3'      (SEQ ID NO. 13)
(Reverse)    5'-GGGCCTCTGCTGAGTACTTG-3'      (SEQ ID NO. 14)
```

FIG. 8 demonstrates that MUC5AC mRNA levels were upregulated by Retinoic acid (RA) in both primary human middle ear epithelial cells (Primary cells) and in the HPV-transformed human middle ear epithelial cell line HMEEC-1). MUC2 expression was upregulated by RA in HMEEC-1, whereas in the primary cultures, the addition of RA had no effect on MUC2 expression. MUC1 and MUC5B mRNA levels did not change in response to RA in either the primary cells or in HMEEC-1.

Surfactant proteins (B and D):

```
Surfactant
B
(Forward)    5'-TCCATCCTCTCTGGTGTGAG-3'      (SEQ ID NO. 15)
(Reverse)    5'-CCTTGACTACGCTGGGGAAT-3'      (SEQ ID NO. 16)

Surfactant
D
(Forward)    5'-AACCATTTACGGAGGCACAG-3'      (SEQ ID NO. 17)
(Reverse)    5'-CAGAACTCGCAGACCACAAG-3'      (SEQ ID NO. 18)
```

FIG. 9 demonstrates that mRNAs for surfactant proteins B and D (SP-B and SP-D) are expressed in both primary human middle ear epithelial cells and in the HPV-transformed human middle ear epithelial cell line HMEEC-1. The SP-B amplification product is 308 base pairs (bp) in length, while that for SP-D is 312 bp long.

Beta Defensins:

```
HBD-1
(Forward)    5'-ATGAGAACTTCCTACCTTCTG CT-3'  (SEQ ID NO.19)
(Reverse)    5'-TCA CTT GCA GCA CTT-3'       (SEQ ID NO.20)

HBD-2
(Forward)    5'-TTTGGTGGTATAGGCGATCC-3'      (SEQ ID NO. 21)
(Reverse)    5'-ATGTCGCACGTCTCTGATGA-3'      (SEQ ID NO. 22)
```

Beta-2 microglobulin
$\beta_2$-Microglobulin (b2M)
(Forward) 5'-CTC GCG CTA CTC TCT CTT TT GG -3'(SEQ NO.23)
(Reverse) 5'-GC TTA CAT GTC TCG ATC CCA CTT AA -3'(ID 24)

Figure 10:
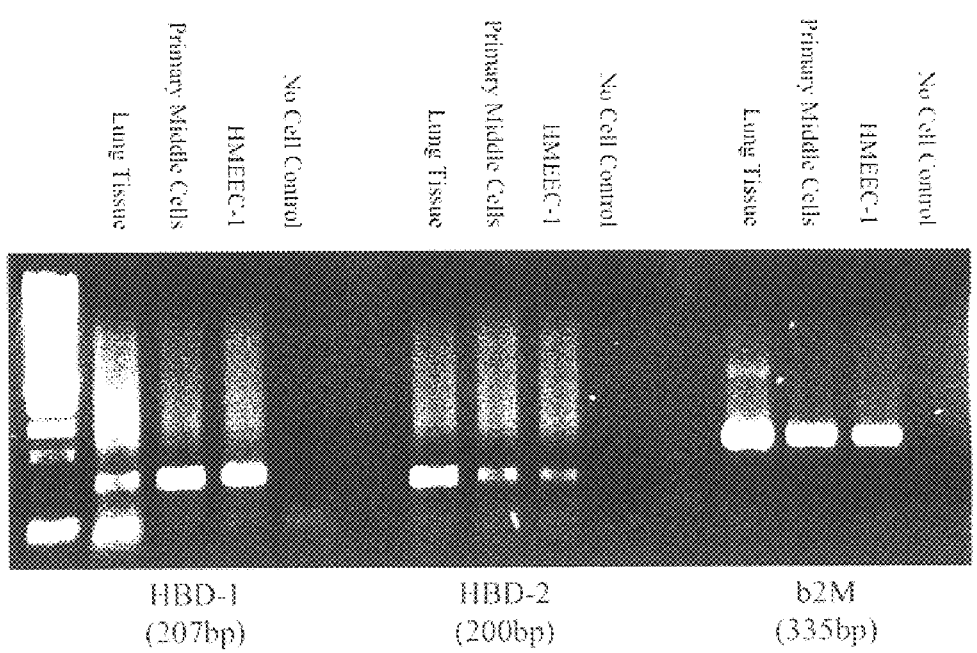
FIG. 10 demonstrates by RT-PCR that mRNAs for the Beta Defensins 1 and 2 (HBD-1 and HBD-2) are expressed in both primary human middle ear epithelial cells and in the HPV-transformed human middle ear epithelial cell line HMEEC-1.

FIG. 10 demonstrates by RT-PCR that mRNAs for the Beta Defensins 1 and 2 (HBD-1 and HBD-2) are expressed in both primary human middle ear epithelial cells and in the HPV-transformed human middle ear epithelial cell line HMEEC-1. The expression of beta-2 microglobulin (b2M) served as a control. The HBD-1 amplification product is 207 base pairs (bp) in length, while that for HBD-2 is 200 bp long. The amplification product for b2M is 335 bp in length.

Example 12

Assay for MEK

FIG. 11 demonstrates that IL-1 alpha activates MEK1/2 (MAPK kinase) in HMEEC-1. Cells were treated with IL-1 alpha for 5, 15 and 45 minutes. The MEK assay was done according to the manufacturer's protocol (PhosphoPlus, MEK1/2 Antibody Kit; New England BioLabs, Beverly, Mass.). Antibodies specific to the phosphorylated (phospho-MEK1/2) and unphosphorylated (MEK1/2) MEK protein were used to distinguish between the phosphorylated and unphosphorylated forms of the protein.

Conclusion

The availability of this unique immortalized human middle ear epithelial cell line of the present invention transformed by two different gene products of human papilloma virus now makes it possible for the first time to determine, not only the various factors and parameters controlling the of expression genes involved in otitis media but also the interaction of pathogens with the middle ear epithelial cells. The cell line can also be used as a screening tool for the identification of chemical and biological agents that may be useful in the therapy of otitis media. This is achieved by standard protocols comparing normal and infected HMEEC cells for growth and inhibition requirements, transcription and translation controlling factors, suppressor elements, cellular enhancer and regulatory proteins, DNA repair, altered metabolism, response to metals, microbial components, biological and chemical agents and the like.

A deposit of one immortalized human middle ear epithelial cell line, designated herein as HMEEC-1 has been made at the American Type Culture Collection (ATCC), 10801 University Boulevard, Manassas, Va. on May 11, 1999 under accession number CRL PTA-81. The deposits shall be viably maintained and replaced if a deposit becomes non-viable during the life of the patent, for a period of 30 years from the date of the deposit, or for years from the last date of request for a sample of the deposit, whichever is longer, and upon issuance of the patent made available to the public without restriction in accordance with the provisions of the Budapest Treaty. The Commissioner of Patents and Trademarks, upon lawful request, shall have access to the deposit.

Although the present invention has been described in considerable detail with reference to certain preferred versions thereof, other versions are possible. Therefore, the spirit and scope of the appended claims should not be limited to the description of the preferred versions described herein.

We claim:

1. A method for producing a non-tumorigenic immortalized cell line that retains phenotypic properties of middle ear epithelial cells, comprising:
   a) providing a primary cell culture of human middle ear epithelial cells;
   b) introducing a polynucleotide encoding an exogenous immortalizing gene into the middle ear epithelial cells;
   c) selecting for immortalized cells that express the exogeous immortalizing gene and retain phenotypic properties of middle ear epithelial cells, said phenotypic properties comprising immunostaining positive for cytokeratins 4, 7, and 18, but not desmin, vimentin, and Factor VIII; contact inhibition; and anchorage dependence.

2. The method of claim 1 wherein the polynucleotide is a subgenomic fragment of a virus, selected from the group consisting of SV40, adenovirus, and human papilloma virus.

3. The method of claim 2, wherein the polynucleotide is a subgenomic fragment of a human papilloma virus, comprising the E6 and E7 genes of said human papilloma virus.

4. The method of claim 3 wherein the human papilloma virus is selected from the group consisting of types 16, 18, 31, 33, and 35.

5. The method of claim 4 wherein the human papilloma virus is type 16.

6. The method of claim 1 wherein the polynucleotide is contained in a viral or plasmid vector.

7. The method of claim 1 wherein the viral vector is selected from the group consisting of retrovirus, adenovirus, and adeno-associated virus vectors.

8. The method of claim 1 wherein the retrovirus vector comprises a replication-defective retrovirus construct.

9. A substantially pure cell line of immortalized non-tumorigenic human middle ear epithelial cells, which expresses an exogenous immortalizing gene and retains phenotypic properties of middle ear epithelial cells, said phenotypic properties comprising immunostaining positive for cytokeratins 4, 7, and 18, but not desmin, vimentin, and Factor VIII; contact inhibition; and anchorage dependence.

10. The cell line of claim 9, wherein the exogenous immortalizing gene is selected from the group consisting of SV40 T antigen, adenovirus EA, and human papilloma virus E6 and E7 genes.

11. The cell line of claim 10 wherein the human papilloma virus is selected from the group consisting of types 16, 18, 31, 33, and 35.

12. A substantially pure cell line of immortalized human middle ear epithelial cells activity expressing the E6 and E7 gene of human papilloma virus 16, wherein the immortalized cell line maintains phenotypic characteristics of human middle ear epithelial cells, said phenotypic characteristics comprising immunostaining positive for cytokeratins 4, 7, and 18, but not desmin, vimentin, and Factor VIII; contact inhibition; and anchorage dependence.

13. The cell line of claim 12, wherein the cell line has human papilloma virus 16 DNA integrated into cellular DNA.

14. The cell line of claim 12, having the phenotypic characteristics of ATCC Accession # CRL PTA-81.

15. A method for determining the effect of a pharmacological agent on cells of the middle ear, said method comprising:
   a) contacting the cell line of claim 9 with said pharmacological agent; and
   b) determining the effect of said pharmacological agent on said cell line.

16. The method of claim 15 wherein the effect is a change in cell growth.

17. The method of claim 15, wherein the effect is a change in a phenotypic characteristic of the cell line.

18. The method of claim 17 wherein the change is an increase or decrease in expression of a cellular gene.

19. The method of claim 18 wherein the cellular gene expresses a gene product selected from the group consisting of bacterial receptors, mucins, aquaporins, cytokines, and growth factors.

20. The method of claim 18 wherein the cellular gene expresses a molecule of innate immunity selected from the group consisting of defensins, surfactant proteins, lysozyme, and lactoferrin.

21. The method of claim 15 wherein the pharmacological agent is selected from the group consisting of chemicals, drugs, hormones, cytokines, and growth factors.

22. A kit for screening a pharmacological agent on middle ear epithelial cells, comprising a container containing the cell line of claim 9.

23. A cell line consisting of ATCC Accession # CRL PTA-81.

24. A method for determining the effect of a pharmacological agent on cells of the middle ear, said method comprising:

a) contacting the cell line of claim 9 with said pharmacological agent; and b) determining the effect of said pharmacological agent on expression of a cellular gene of said cell line, wherein said cellular gene is selected from the group consisting of bacterial receptors, mucins, aquaporins, cytokines, defensins, surfactant proteins, lysozyme, and lactoferrin.

* * * * *